(12) United States Patent
Lewandowski et al.

(10) Patent No.: US 7,659,323 B2
(45) Date of Patent: Feb. 9, 2010

(54) HYDROPHILIC GEL FROM REACTIVE HYDROPHILIC OLIGOMERS

(75) Inventors: Kevin M. Lewandowski, Inver Grove Heights, MN (US); Duane D. Fansler, Dresser, WI (US); Michael S. Wendland, North St. Paul, MN (US); Steven M. Heilmann, Afton, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/555,354

(22) Filed: Sep. 8, 2009

(65) Prior Publication Data

US 2009/0326498 A1 Dec. 31, 2009

Related U.S. Application Data

(60) Division of application No. 12/264,516, filed on Nov. 4, 2008, now Pat. No. 7,598,298, which is a division of application No. 11/463,103, filed on Aug. 8, 2006, now Pat. No. 7,459,489, which is a continuation-in-part of application No. 10/672,580, filed on Sep. 26, 2003, now abandoned.

(51) Int. Cl.
C08F 2/46 (2006.01)
C08F 20/26 (2006.01)

(52) U.S. Cl. .................... 522/181; 522/34; 522/35; 522/173; 522/182; 525/308; 525/309; 424/445; 424/448

(58) Field of Classification Search .............. 522/34, 522/35, 173, 181, 182; 525/308, 309; 424/445, 424/448
See application file for complete search history.

(56) References Cited

U.S. PATENT DOCUMENTS

| RE24,906 | E | 12/1960 | Ulrich |
|---|---|---|---|
| 3,121,021 | A | 2/1964 | Copeland |
| 3,389,827 | A | 6/1968 | Abere et al. |
| 4,094,842 | A | 6/1978 | Wenzel et al. |
| 4,112,213 | A | 9/1978 | Waldman |
| 4,123,423 | A | 10/1978 | Wenzel et al. |
| 4,190,566 | A | 2/1980 | Noll et al. |
| 4,385,164 | A | 5/1983 | Sinclair et al. |
| 4,499,896 | A | 2/1985 | Heinecke |
| 4,598,004 | A | 7/1986 | Heinecke |
| 4,680,352 | A | 7/1987 | Janowicz et al. |
| 4,694,054 | A | 9/1987 | Janowicz |
| 4,849,458 | A | 7/1989 | Reed et al. |
| 5,362,826 | A | 11/1994 | Berge et al. |
| 5,506,279 | A | 4/1996 | Babu et al. |
| 5,531,855 | A | 7/1996 | Heinecke et al. |
| 5,614,310 | A | 3/1997 | Delgado et al. |
| 5,653,699 | A | 8/1997 | Reed et al. |
| 5,733,570 | A | 3/1998 | Chen et al. |
| 5,738,642 | A | 4/1998 | Heinecke et al. |
| 5,741,543 | A | 4/1998 | Winslow et al. |
| 5,773,534 | A | 6/1998 | Antonelli et al. |
| 5,849,325 | A | 12/1998 | Heinecke et al. |
| 5,902,836 | A | 5/1999 | Bennett et al. |
| 6,007,833 | A | 12/1999 | Chudzik et al. |
| 6,171,985 | B1 | 1/2001 | Joseph et al. |
| 6,198,016 | B1 | 3/2001 | Lucast et al. |
| 6,221,303 | B1 | 4/2001 | Steinmann |
| 6,361,768 | B1 | 3/2002 | Galleguillos et al. |
| 6,448,301 | B1 | 9/2002 | Gaddam et al. |
| 6,461,467 | B2 | 10/2002 | Blatchford et al. |
| 6,559,223 | B2 | 5/2003 | Green et al. |
| 6,635,690 | B2 | 10/2003 | Heilmann et al. |
| 6,664,306 | B2 | 12/2003 | Gaddam et al. |
| 7,005,143 | B2 | 2/2006 | Abuelyaman et al. |
| 7,015,286 | B2 | 3/2006 | Heillmann et al. |
| 7,074,839 | B2 | 7/2006 | Fansler et al. |
| 7,148,265 | B2 | 12/2006 | Barr et al. |
| 7,276,247 | B2 | 10/2007 | Fansler et al. |
| 7,342,047 | B2 | 3/2008 | Lewandowski et al. |
| 7,384,984 | B2 | 6/2008 | Lewandowski et al. |
| 7,459,489 | B2 | 12/2008 | Lewandowski et al. |
| 7,598,298 | B2 | 10/2009 | Lewandowski et al. |
| 2005/0070688 | A1 | 3/2005 | Lewandowski et al. |
| 2006/0165762 | A1 | 7/2006 | Plaut et al. |

FOREIGN PATENT DOCUMENTS

| WO | WO 99/13865 | 3/1999 |
|---|---|---|
| WO | WO 99/13866 | 3/1999 |
| WO | WO 00/42958 | 7/2000 |

(Continued)

OTHER PUBLICATIONS

Gladyshev, G.P. et al., "Polymerization at Advanced Degrees of Conversion", Keter Press, Jerusalem (1970).

(Continued)

*Primary Examiner*—Helen L. Pezzuto
(74) *Attorney, Agent, or Firm*—Kent S. Kokko

(57) ABSTRACT

Hydrophilic compositions are described, which are prepared from a first oligomer containing pendent polymerizable groups and pendent hydrophilic groups, crosslinked with a co-reactive second component oligomer possessing photoinitiator groups. The compositions may be used as in preparation of hydrophilic gel coatings or layers for medical devices.

20 Claims, No Drawings

FOREIGN PATENT DOCUMENTS

| | | |
|---|---|---|
| WO | WO 01/18079 | 3/2001 |
| WO | WO 01/60296 | 8/2001 |
| WO | WO 03/086493 | 10/2003 |
| WO | WO 2005/035607 | 4/2005 |

OTHER PUBLICATIONS

Nguyen et al., "Photopolymerizable Hydrogels for Tissue Engineering Applications", Biomaterials, (2002), pp. 4307-4314, vol. 23, Elsevier Science Ltd.

Odian, G., "Principles of Polymerization", 3rd edition, 1991, John Wiley & Sons: New York, p. 19-24, 108 (1991).

Scott et al., "Highly Crosslinked, PEG-Containing Copolymers for Sustained Solute Delivery", Biomaterials, (1999), pp. 1371-1380, vol. 20, Elsevier Science Ltd.

Protective Groups in Organic Synthesis, T. Greene and P.G.M. Wuts, Eds., 3$^{rd}$ edition, Wiley Interscience, New York, N.Y., 1999.

HYDROPHILIC GEL FROM REACTIVE HYDROPHILIC OLIGOMERS

CROSS REFERENCE TO RELATED APPLICATIONS

This application is a divisional of U.S. application Ser. No. 12/264,516, filed Nov. 4, 2008 now U.S. Pat. No. 7,598,298; which is a divisional of U.S. application Ser. No. 11/463,103, filed Aug. 8, 2006, now U.S. Pat. No. 7,459,489; which is a continuation in part of U.S. application Ser. No. 10/672,580, filed Sep. 26, 2003, now abandoned, the disclosure of which is herein incorporated by reference.

TECHNICAL FIELD OF THE INVENTION

This invention relates to novel hydrophilic, crosslinkable oligomer compositions and articles prepared therefrom. The compositions can be useful in preparing gel materials and medical articles incorporating such materials, particularly medical articles useful as wound dressings.

BACKGROUND OF THE INVENTION

Historically, exudate from a wound has been treated by absorbing it using a dressing containing an absorbent material. Such dressings have contained a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

More recently the use of so-called "occlusive" dressings for pressure sores and ulcers has gained acceptance. Most of these products are formed from several layers, including at least an inner skin-contacting layer and an outer backing layer. The dressing is applied as a cover for the sore or ulcer in a size providing a margin around the wound area that adhesively seals to the skin. An inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

A wound care product in current use utilizes a hydrocolloid absorbent. Such a material typically has poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

SUMMARY OF THE INVENTION

Though there are known hydrophilic gel materials useful in medical applications such as wound dressings, many do not have the appropriate balance of absorption and cohesive strength. Thus, additional such materials are needed. Further, it can be desirable to provide an occlusive material that is also transparent and/or flexible for use in a medical article such as a wound dressing or wound packing material. Yet further, it can be desirable to provide compositions that are melt-processible.

The current invention describes reactive, melt-processible materials that may be cast on a web and cured by a chain-growth mechanism to yield uniform coatings, particularly gel coatings. The component oligomers and extent of reaction, or crosslink density, can be varied in order to provide specific properties for a range of applications. The molecular weight of these materials is such that they can easily be processed, giving economic and/or environmental advantages. The materials can be subsequently cured through application of actinic energy, such as UV radiation, to yield improved final mechanical properties. Thus, these materials represent a significant advance of the current art.

Briefly, the present invention provides novel hydrophilic, oligomeric compositions prepared from a first oligomer containing pendent hydrophilic groups and pendent polymerizable functional groups, and a co-reactive second component oligomer having pendent photoinitiator groups. The second component oligomer may further comprise polymerizable monomer units having pendent hydrophilic groups. The compositions can be melt-processible.

In one aspect this invention provides a hydrophilic, crosslinkable, oligomeric composition comprising:

(a) a first component oligomer comprising a plurality of polymerized monomer units having pendent, free-radically polymerizable functional groups, and pendent, hydrophilic poly(alkylene oxide) groups; and (b) a second component oligomer comprising a plurality of polymerized monomer units having pendent, photoinitiator groups.

This invention can have one or more of several advantages. The invention provides a UV crosslinkable composition that produces no or minimal by-products, and that achieves its crosslink density by chain-growth addition. The composition is low in viscosity, readily melt processible and coatable, and has minimal residuals content such as solvents, monomers, plasticizers, by-products of condensation reactions or displacement reactions and/or viscosity modifiers. The compositions can be rapidly and reliably prepared without requiring specialized equipment and without generating concerns about potentially toxic or irritating unreacted low molecular weight monomeric species.

In another aspect, this invention provides a process for making a substrate bearing a coating of a crosslinked composition (such as a hydrophilic gel) on at least one surface thereof, comprising the steps of:

(a) coating the crosslinkable, oligomeric composition of the invention, containing an initiator onto a substrate, and (b) subjecting the coated crosslinkable composition to sufficient actinic energy to crosslink said composition.

For performance, environmental, and economic considerations, photoinitiated polymerization is a particularly desirable method for preparing a coating, such as a gel layer directly on the substrate. With this polymerization technique, it is advantageous to create a composition having coatable viscosity of 10,000 centipoise or less (when measured at or below 100° C.), coat the composition on the substrate, then crosslink the components to build strength.

As used herein, the term "melt processible" or simply "processible" is used to refer to polymer compositions that possess or achieve a suitable low viscosity for coating or extrusion at temperatures less than the decomposition temperature(s) of the oligomers and less than the temperature at which premature gelation occurs, using conventional extrusion equipment without the need for addition of solvents, monomers, plasticizers and/or viscosity modifiers and without the need for extraordinary pressures. Preferably the composition is melt processable at temperatures less than or equal to 100° C.

In one embodiment, this invention provides absorbent medical articles and hydrophilic, polymeric gel materials for use therein, which are preferably transparent. By "gel" (or "polymer gel" or "polymeric gel material" or "hydrophilic gel"), it is meant a gel material capable of swelling on contact with (or water-based fluids such as body fluids including blood, plasma, and intracellular fluid or fluids similar to body fluids such as physiological saline), but does not dissolve in water. The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is capable of absorbing fluids, particularly body fluids and preferably moderate to heavy amounts of body fluids, while retaining its structural integrity (i.e., remaining sufficiently intact such that it can perform the function of acting as a wound dressing, for example).

Preferably the gel material is transparent and retains its transparency after absorption of fluids. By "transparent", it is meant that when the preferred material is applied to a patient (e.g., at a wound site), the area underlying the dressing can be visualized sufficiently to permit observation of the wound by a health care worker.

The term hydrophilic is used herein to describe oligomer compositions, which are capable of absorbing water exposed thereto in significant quantity, typically more than about 50% by weight, preferably 100% by weight, more preferably more than 200% by weight.

The application of hydrophilic polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, "medical" applications encompass dental applications, including dental adhesives, restoratives, coatings, composites, sealants, etc. Because water swelling polymer gels have compositions and mechanical properties similar to those of biological tissues, such gels may be applied in a wide variety of fields in the future.

The ability to vary the crosslink density permits the modification of properties suitable for the various applications described previously. The novel compositions of the present invention cure to form crosslinked compositions possessing tailorable properties such as shear, peel, release, strength, hardness, elasticity, absorbancy and toughness, for example, through selection of the particular constituents, and by control of the crosslink density. While the requirements for medical gels and flexible coatings, for example, are very different, the structure of the material and density of linkages can be altered while still maintaining the same method of forming crosslinked compositions. The maximum crosslink density is predetermined by the percentage of polymerizable functional groups of the first component oligomer and the percentage of photoinitiator groups of the second component oligomer incorporated into the crosslinkable composition. It may also be desirable to partially convert or cure a system for improved processing, while using a subsequent curing stage to obtain final properties.

As used herein, the term "crosslinking" means the formation of a polymeric network of infinite molecular weight and occurs in polymerizations with oligomeric reactants having functionalities greater than two. Additional information may be found in G. Odian, Principles of Polymerization, 3rd edition, 1991, John Wiley & Sons: New York, p. 108. A crosslink is formed between the pendent polymerizable functional groups by a chain growth process.

Advantageously, the present invention provides crosslinkable compositions that are readily processed without appreciable residual content such as solvents, monomers, plasticizers and/or viscosity modifiers, and which do not contain byproducts from condensation or displacement reactions. Curable systems containing residual content can give rise to a significant increase in density when transformed from the uncured to the cured state causing a net shrinkage in volume. As is well known, shrinkage can cause a general loss of adhesion in many instances as well as significant movement and unpredictable registration. Shrinkage can also create residual stress in coatings, which can subsequently lead to mechanical failure.

The composition of the present invention minimizes shrinkage due to solvent evaporation and/or monomer polymerization. The low shrinkage compositions of this invention are particularly useful in dental, molding applications or in any applications where accurate molding and/or registration are required. The present invention provides a new class of reactive oligomers that may be formulated as 100% solids, melt processed, cured by actinic radiation means and that exhibit properties that meet or exceed those of solvent-borne or syrup polymers. The present invention provides compositions that exhibit less than 2% shrinkage, and preferably less than 1%.

Further, the purity of the materials and clean environment for processing are also important to produce high performance materials. Polymers used for coatings and gels are often desirably delivered without significant amounts of volatile materials (such as monomeric species) to eliminate any contamination. However, the problems of residual volatile materials constitute a much more formidable challenge especially when acceptable limits of migratable, volatile impurities are on the order of a few parts per million. Industries such as medical and food packaging require materials of high purity and lower cost. The composition of the present invention avoids problems due to residuals contamination, having a residuals content of less than 2 wt. %, preferably less than 1 wt. %.

DETAILED DESCRIPTION OF THE INVENTION

The present invention provides crosslinkable compositions useful in the preparation of hydrophilic gels. The compositions are prepared from oligomers having pendent polymerizable functional groups and are formed from ethylenically unsaturated monomers. The composition comprises:

(a) a first component oligomer comprising a plurality of polymerized monomer units having pendent, free-radically polymerizable functional groups, and a plurality of polymerized monomer units having pendent, hydrophilic poly(alkylene oxide) groups; and (b) a second component oligomer comprising a plurality of polymerized monomer units having pendent, photoinitiator groups and a plurality of polymerized monomer units having pendent, hydrophilic poly(alkylene oxide) groups.

The composition comprises, per 100 parts by weight of a first component, a sufficient amount of said second component to provide greater than two crosslinks per first component oligomer chain when cured or crosslinked. The relative amounts of said first and second component oligomers may vary widely; i.e., from 0.1 to 99.9 parts by weight of the first component oligomer and from 0.1 to 99.9 parts by weight of the second component oligomer. However, the relative amounts are chosen so that the crosslinked composition is hydrophilic, i.e., absorbs at least 50 wt. % water.

In one embodiment the first oligomer component (a) comprises:

(a) from 20 to 99 parts by weight of polymerized monomer units derived from an ethylenically-unsaturated monomer having a poly(alkylene oxide) group;

(b) from 0.1 to 35 parts by weight of polymerized monomer units derived from an ethylenically-unsaturated monomer having a pendent polymerizable group;

(c) from 0 to 50 parts by weight of polymerized monomer units derived from polar monomer;

(d) from 0 to 20 parts by weight of polymerized monomer units derived from hydrophobic monomers; and (e) from 0 to 10 parts by weight of at least one other monomer.

In one embodiment, the second component oligomer comprises:

(a) from 0.01 to 99.99 parts by weight of polymerized units of free radically polymerizable; and (b) from 99.99 to 0.01 parts by weight of polymerized monomer units derived from an ethylenically-unsaturated monomer having a pendent photoinitiator group.

Preferably the free radically polymerizable monomers of the second component oligomer are (meth)acryloyl monomers. It will be understood with respect to the above formula, that the oligomeric photoinitiator may have a photoinitiator group on essentially each repeat unit of the oligomer (i.e., >90% of the repeat units).

In a preferred embodiment the second oligomer component comprises:

(a) from 20 to 99 parts by weight, preferably 50 to 99 parts by weight, of polymerized monomer units having pendent, hydrophilic poly(alkylene oxide) groups, and (b) from 0.1 to 25 parts by weight, preferably 0.1 to 10 parts by weight, of polymerized monomer units derived from an ethylenically-unsaturated monomer having a pendent photoinitiator group;

(c) from 0 to 25 parts by weight, preferably 0.1 to 10 parts by weight, of polymerized monomer units derived from an ethylenically-unsaturated monomer having a pendent polymerizable group;

(d) from 0 to 20 parts by weight, preferably less than 10 parts by weight, of hydrophobic monomers, such as polymerized monomer units derived from (meth)acrylic acid esters, preferably of non-tertiary alkyl alcohols containing 1-14 carbon atoms;

(e) from 0 to 50 parts by weight of polymerized monomer units derived from a polar monomer; and (f) from 0 to 40 parts by weight, preferably less than 25 parts by weight, of at least one other monomer (described below).

The first and second component oligomers comprise polymerized monomer units derived from an ethylenically-unsaturated monomer having pendent poly(alkylene oxide) group of the formula: Z-Q-(CH($R^1$)—CH-Q)-$R^2$, wherein Z is a polymerizable ethylenically unsaturated moiety, $R^1$ is a H or a $C_1$ to $C_4$ alkyl group, $R^2$ is a H, a $C_1$ to $C_4$ alkyl group, aryl group, or combinations thereof and m is from 2 to 100, preferably 5 to 20, and Q is a divalent linking group selected from —O—, —$NR^1$—, —CO— and —$CONR^1$. In one embodiment, the poly(alkylene oxide) group is a poly(ethylene oxide) (co)polymer. In another embodiment, the pendent poly(alkylene oxide) group is a poly(ethylene oxide-co-propylene oxide) copolymer. Such copolymers may be block copolymers, random copolymers, or gradient copolymers.

Useful ethylenically unsaturated moiety, Z, of the monomer may include:

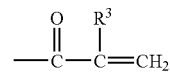

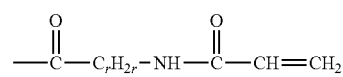

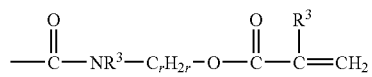

—CH=$CH_2$, and —$C_rH_{2r}$—CH=$CH_2$ wherein $R^3$ is H or Me and r=1-10.

The monomer having a poly(alkylene oxide) group can be prepared, for example, by reacting mono- or di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxy groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl(meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

The first and optionally the second component oligomers of the composition comprise one or more pendent groups that include free-radically polymerizable unsaturation, including (meth)acryloyl, (meth)acryloxy, propargyl, vinyl, allyl, acetylenyl and (meth)acrylamido. Such pendent groups can be incorporated into the oligomer in at least two ways. The most direct method is, for example, to include among the monomer units monomers having two or more free radically polymerizable groups, preferably of differing reactivity.

Using the "direct method" of incorporating the pendent, free-radically polymerizable functional group, useful functional monomers include those unsaturated aliphatic, cycloaliphatic, and aromatic compounds having up to about 36 carbon atoms that include a functional group capable of free radical addition such as those groups containing a carbon-carbon double bond including vinyl, vinyloxy, (meth) acrylic, (meth)acrylamido, and acetylenic functional groups.

Examples of polyethylenically unsaturated monomers that can be used include, but are not limited to, polyacrylic-functional monomers such as ethylene glycol diacrylate, propylene glycol dimethacrylate, bisphenol-A di(meth)acrylate, trimethylolpropane triacrylate, 1,6-hexanedioldiacrylate, pentaerythritol di-, tri-, and tetraacrylate, and 1,12-dodecanedioldiacrylate; olefinic-acrylic-functional monomers such as allyl methacrylate, 2-allyloxycarbonylamidoethyl methacrylate, and 2-allylaminoethyl acrylate; allyl 2-acrylamido-2,2-dimethylacetate; divinylbenzene; vinyloxy group-substituted functional monomers such as 2-(ethenyloxy)ethyl (meth)acrylate, 3-(ethynyloxy)-1-propene, 4-(ethynyloxy)-1-butene, and 4-(ethenyloxy)butyl-2-acrylamido-2,2-dimethylacetate, and the like. Useful polyunsaturated monomers, and useful reactive/co-reactive compounds that may be used to prepare a polymer having pendent unsaturation are described in greater detail in U.S. Pat. No. 5,741,543 (Winslow et al.), incorporated in its entirety herein by reference.

Preferred polyunsaturated monomers are those where the unsaturated groups are of unequal reactivity. Those skilled in the art recognize that the particular moieties attached to the unsaturated groups affect the relative reactivities of those unsaturated groups. For example, where a polyunsaturated monomer having unsaturated groups of equal reactivity (e.g., HDDA) is used, premature gelation of the composition must be guarded against by, for example, the presence of oxygen, which acts as a radical scavenger. Conversely, where a polyunsaturated monomer having unsaturated groups of differing reactivities is used, the more reactive group (such as (meth) acrylate as (meth)acrylamido) preferentially is incorporated into the oligomer backbone before the less reactive unsaturated group (such as vinyl, allyl, vinyloxy, or acetylenic) reacts to crosslink the composition. The direct method is generally not preferred due to difficulty in control of branching and premature gellation.

An indirect, but preferred, method of incorporating pendent groups that comprise polymerizable unsaturation into the first and second oligomers is to include among the monomer units of the oligomer some that comprise a reactive functional group. Useful reactive functional groups include, but are not limited to, hydroxyl, amino, oxazolonyl, oxazolinyl, acetoacetyl, azlactonyl, carboxyl, isocyanato, epoxy, aziridinyl, acyl halide, and cyclic anhydride groups. Preferred among these are carboxyl, hydroxyl, amino, azlactonyl and aziridinyl groups. These pendent reactive functional groups are reacted with unsaturated compounds that comprise functional groups that are co-reactive with the reactive pendent functional group. When the two functional groups react, an oligomer with pendent unsaturation results. In some applications, it may be desirable to use less than a stoichiometric equivalent of unsaturated compounds that comprise co-reactive functional groups, so that some of the pendent functional group remain unreacted.

Using the "indirect method" of incorporating the pendent, free-radically polymerizable functional groups, useful reactive functional groups include hydroxyl, secondary amino, oxazolinyl, oxazolonyl, acetyl, acetonyl, carboxyl, isocyanato, epoxy, aziridinyl, acyl halide, vinyloxy, and cyclic anhydride groups. Where the pendent reactive functional group is an isocyanato functional group, the co-reactive functional group preferably comprises a secondary amino or hydroxyl group. Where the pendent reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophile and electrophic functional groups.

Representative examples of useful monomers having reactive functional groups include hydroxyalkyl(meth)acrylates such as 2-hydroxyethyl(meth)acrylate, 3-hydroxypropyl (meth)acrylate, 2,3-dihydroxypropyl(meth)acrylate, 4-hydroxybutyl (meth)acrylate and 2-(2-hydroxyethoxy)ethyl (meth)acrylate; aminoalkyl(meth)acrylates such as 3-aminopropyl(meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl(meth)acrylate; epoxy-substituted compounds such as glycidyl(meth)acrylate; aziridinyl-substituted compounds such as N-acryloylaziridine and 1-(2-propenyl)-aziridine; and acryloyl halides such as (meth)acryloyl chloride.

Preferred functional monomers have the general formula:

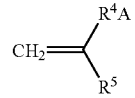

wherein $R^5$ is hydrogen, a $C_1$ to $C_4$ alkyl group, or a phenyl group, preferably hydrogen or a methyl group; $R^4$ is a single bond or a divalent linking group that joins an ethylenically unsaturated group to a reactive functional group "A" and preferably contains up to 34, preferably up to 18, more preferably up to 10, carbon and, optionally, oxygen and nitrogen atoms and, when $R^4$ is not a single bond, is preferably selected from

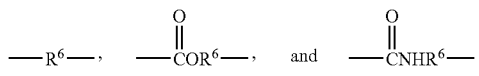

in which $R^6$ is an alkylene group having 1 to 6 carbon atoms, a 5- or 6-membered cycloalkylene group having 5 to 10 carbon atoms, or an alkylene-oxyalkylene in which each alkylene includes 1 to 6 carbon atoms or is a divalent aromatic group having 6 to 16 carbon atoms; and A is a functional group, capable of reacting with a co-reactive functional group for the incorporation of a free-radically polymerizable functional group.

Ethylenically unsaturated monomers that comprise a radiation-sensitive group, preferably an α-cleavage-type photoinitiator group and that are copolymerizable with the described free radically-polymerizable ethylenically unsaturated monomers (hereinafter "photoinitiator monomers") constitute from 0.01 to about 5 pbw, preferably 0.01 to 3 pbw, of the crosslinkable composition. Preferred photoinitiator monomers include free-radically polymerizable, ethylenically unsaturated compounds having the functionality represented by the structure:

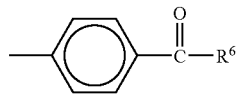

wherein $R^6$ is

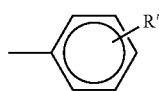

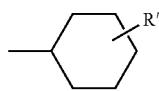

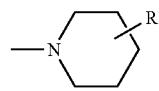

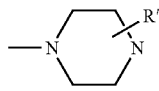

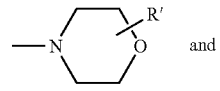 and

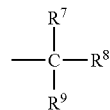

wherein R' is H or a C1 to C4 alkyl group, $R^7$, $R^8$, and $R^9$ are independently a hydroxyl group, a phenyl group, a C1 to C6 alkyl group, or a C1 to C6 alkoxy group.

The photoinitiator monomers may be prepared by the reaction between a polymerizable monomer having a reactive functional group with a photoinitiator compounds having a co-reactive functional group. Representative examples of useful polymerizable monomers having a reactive functional group include hydroxyalkyl (meth)acrylates such as 2-hydroxyethyl(meth)acrylate and 2-(2-hydroxyethoxy)ethyl (meth)acrylate; aminoalkyl(meth)acrylates such as 3-aminopropyl(meth)acrylate and 4-aminostyrene; oxazolinyl compounds such as 2-ethenyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl(meth)acrylate and 4-isocyanatocyclohexyl (meth)acrylate; epoxy-substituted compounds such as glycidyl(meth)acrylate; aziridinyl-substituted compounds such as N-acryloylaziridine and 1-(2-propenyl)-aziridine; and acryloyl halides such as (meth)acryloyl chloride.

Representative examples of photoinitiator compounds having a co-reactive functional group include compounds such as 1-(4-hydroxyphenyl)-2,2-dimethoxyethanone, 1-[4-(2-hydroxyethyl)phenyl]-2,2-dimethoxyethanone, (4-isocyanatophenyl)-2,2-dimethoxy-2-phenylethanone, 1-{4-[2-(2, 3-epoxypropoxy)phenyl]}-2,2-dimethyl-2-hydroxyethanone, 1-[4-(2-aminoethoxy)phenyl]-2,2-dimethoxyethanone, and 1-[4-(carbomethoxy)phenyl]-2,2-dimethoxyethanone. Such photoinitiator monomers (and polymeric photoinitiators derived therefrom) are described, for example, in U.S. Pat. Nos. 5,902,836 (Babu et al.) and 5,506,279 (Babu et al.), the disclosures of which are herein incorporated by reference.

Preferred photoinitiators are photoactive compounds that undergo a Norrish I cleavage to generate free radicals that can initiate by addition to the acrylic double bonds. Norrish type 1 photocrosslinkers, especially α-cleavage type photoinitiators, are preferred.

The first component oligomer, and optionally the second component oligomer may comprise one or more polar monomers. As used herein "polar monomers" are those polymerizable monomers having a water miscibility (water in monomer) of at least 1 wt. %, preferably at least 5 wt. % without reaching a cloud point and are exclusive of the poly(alkylene oxide) monomer. The first and second component oligomers optionally comprise from 0 to 50 parts by weight of such polar monomers.

Polar monomers can be used to increase the absorbency and/or improve the mechanical properties (e.g., the tensile strength) of the crosslinked polymer used in forming the gel material. Preferred polar monomers can also provide compliance to the resultant polymer. Examples of suitable polar monomers include 2-hydroxyethyl(meth)acrylate (HEMA), 2-hydroxypropyl(meth)acrylate, 3-hydroxypropyl(meth) acrylate, 2,3-dihydroxypropyl(meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, (meth)acrylic acid, itaconic acid, beta-carboxyethyl acrylate, glycerol methacrylate, [2-(meth)(acryloyloxy)ethyl]trimethylammonium chloride, [2-(meth)(acryloyloxy)ethyl]trimethylammonium methyl sulfate, and combinations thereof. Preferred polar monomers include 2-hydroxyethyl(meth)acrylate (HEMA) N-vinyl pyrrolidone, N-vinyl acetamide, and mixtures thereof, and the like.

The first and second oligomers may further comprise hydrophobic monomers. Hydrophobic monomers can be used to reduce (and thereby better control) the absorbency of the polymer used in forming the gel material, and preferably improve the strength of the polymer.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_5$-$C_{30}$ alkyl groups. Due to T and sidechain crystallinity considerations, preferred are those having from $C_5$-$C_{12}$ alkyl groups, although use of $C_1$-$C_4$ and C13-$C_{14}$ alkyl groups are also useful if the combinations provide a molecule averaged number of carbon atoms between $C_5$ and $C_{12}$. However, for many applications, $C_{12}$-$C_{30}$ alkyl groups may be preferred. Useful specific examples of alkyl acrylate esters include: methyl acrylate, ethyl acrylate, n-propyl acrylate, 2-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acryamides include mono- and diacryamides having pentyl, hexyl, heptyl, isobornyl, octyl, 2-ethylhexyl, isononyl, decyl, undecyl, dodecyl, tridecyl, and tetradecyl groups may be used.

The first and second component oligomers may further comprise other monomers. The selection of the "other monomers" useful in preparing the functional oligomer(s) (of the first and second components) is such that the ultimate crosslinked material has properties suitable for its application. For example, "other monomers" may be used to increase the tensile strength or other mechanical properties, or to control the T of the polymer.

Representative examples of "other monomers" include free-radically polymerizable polar monomers having at least one ethylenically unsaturated polymerizable group that are copolymerizable with the aforementioned monomers, and include vinyl monomers such as vinyl acetate, styrenes, allyl ethers, maleic anhydride, and alkyl vinyl ethers.

Preferred first and second component oligomers used in forming the gel materials of the present invention include 20 to 99 parts by weight of the monomer units having a poly(alkylene oxide) group. More preferably, the first component oligomer comprises 50 to 99 parts by weight and most preferably 60 to 99 parts by weight of the monomer units having a poly(alkylene oxide) group.

Preferred first and optionally second component oligomers of the present invention include 0.1 to 35 parts by weight of the monomer units having a pendent polymerizable functional group. More preferably, the first component oligomers comprise 0.5 to 35 parts by weight, and most preferably 0.5 to 5 parts by weight of the monomer units having a pendent polymerizable functional group.

Preferred first and second component oligomers of the present invention may comprise 0 to 50 parts by weight of a polar monomer. More preferably, the polar monomer is used in an amount of no greater than about 35 parts by weight, based on the total weight of the oligomer. Most preferably, the polar monomer is used in an amount of no greater than about 30 parts by weight. Preferably, the polar monomer is used in an amount of at least about 5 parts by weight. More preferably, the polar monomer is used in an amount of at least about 10 parts by weight.

Preferred first and second component oligomers of the present invention include no greater than about 20 parts by weight of a hydrophobic monomer. Even more preferably, the hydrophobic monomer is used in an amount of no greater than about 10 parts by weight. Most preferably, the hydrophobic monomer is used in an amount of no greater than about 5 parts by weight of a hydrophobic monomer.

Preferred first and second component oligomers of the present invention include no greater than about 10 parts by weight of "other monomers", based on the total weight of the oligomer. More preferably, the hydrophobic monomer is used in an amount of less than 5 parts by weight, based on the total weight of the oligomer.

It will be understood in the context of the above description of the first and second oligomers, that the amount of monomer units having pendent poly(alkylene oxide) groups in the first and second component oligomers, and the relative amounts of the first and second component oligomers is such that the cured composition is hydrophilic, as previously defined.

It will be understood in the context of the above description of the first and second oligomers, that the ethylenically-unsaturated monomer possessing a free-radically polymerizable group is chosen such that it is free-radically polymerizable with itself (i.e., with another ethylenically-unsaturated functional group on the first, or optionally the second, component oligomer) and with the pendent photoinitiator group of the second component oligomer. The reactions between pendent, unsaturated functional groups provide a crosslink by forming a covalent bond by free radical addition reactions of ethylenically-unsaturated groups between oligomeric compounds. The pendent functional groups react by a reaction in which no by-product molecules are created (unlike condensation and displacement reactions), and the exemplified reaction partners react by this preferred mode.

Where the crosslinkable composition is to be processed using high temperatures and the direct method of including pendent unsaturation has been used, care must be taken not to activate those pendent unsaturated groups and cause premature gelation. For example, hot-melt processing temperatures can be kept relatively low and polymerization inhibitors can be added to the mixture. Accordingly, where heat is to be used to process the composition, the above-described indirect method is the preferred way of incorporating the pendent unsaturated groups.

Oligomers of the first and second components have relatively low molecular weight, then build molecular weight (and strength) by a chain-growth process of the oligomers, through the pendent polymerizable functional groups. As result of the relatively low molecular weight, the oligomers are easily processible in operations such as coating, spraying, extrusion and molding, because of the low melt viscosity prior to crosslinking, and without the need for residuals, such as solvents, plasticizers or viscosity modifiers. With the present oligomers, the slope of the log-log plot of viscosity vs. molecular weight ($M_n$) is about 1, whereas for higher molecular weight polymers the slope is 3.4. The oligomers of the present invention provide processibility, and then crosslinking of the oligomers provides the needed physical properties such as toughness, hardness, tensile strength and others that are manifested in the cured state. Unless otherwise indicated molecular weight will refer to number average molecular weight.

A composition comprising oligomers of the first and second components have an average degree of polymerization (DP) generally less than about 300. The greater than expected viscosity (for polymers having a degree of polymerization greater than 300), is attributed to entanglements of polymer chains. It has been shown empirically that polymers or oligomers with less than 300 repeat units are not entangled. Prior to the present invention, unentangled polymers have been shown to be processible but they have low strength. Preferably, both the first and second component oligomers have a degree of polymerization less than about 300.

If desired, higher molecular weight polymers may be blended with lower molecular weight oligomers so that the mixture has a viscosity of 500 to 10,000 cPs at temperatures less than 100° C.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art. Useful chain transfer agents also include cobalt chelates, as described in U.S. Pat. Nos. 4,680,352 and 4,694,054, and oligomeric chain transfer agents as exemplified by

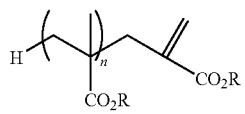

wherein each R is a lower alkyl group or a functional group (as previously described) and n is a number typically less than 10, as described in U.S. Pat. Nos. 5,362,826 and 5,773,534.

As previously described, the composition of the present invention comprises a first oligomer component with a plurality of pendent polymerizable functional groups and pendent hydrophilic groups, a second component with a plurality of pendent co-photoinitiator groups. The physical form of the composition may be a viscous liquid, a low melting solid or a powder, which is related to the glass transition temperature and the molecular weight. The amount of each monomer component and the relative amounts of the first and second component oligomers may be adjusted to obtain compositions having desired hydrophilicity, melt-processibility and mechanical properties.

The oligomers used in forming the gel material of the present invention can be produced by polymerizing the above-described monomers by conventional polymerization methods. Typical polymerization methods that can be used include thermal and/or photochemical as well as bulk and solution polymerization.

In a typical solution polymerization method, a monomer mixture is heated with stirring in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and 2,2'-azobisisobutyronitrile. Those polymerization initiators can be used alone or as mixtures thereof.

In a typical photopolymerization method, a monomer mixture is irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 184 and 2959.

These photo- and thermal initiators can be employed in concentrations ranging from about 0.0001 to about 3.0 pbw, preferably from about 0.001 to about 1.0 pbw, and more preferably from-about 0.005 to about 0.5 pbw, per 100 pbw of the monomer composition.

Liquid oligomers may be obtained if the glass transition temperature of the oligomer component is below ambient temperature and the molecular weight of the oligomer component is below entanglement molecular weight (i.e., a degree of polymerization of less than about 300). Low melting solids may be obtained when the $T_g$ is at or below ambient temperature. Powders may be obtained when the $T_g$ is above ambient temperature. Due to the amount of poly(alkylene oxide) in the oligomers the oligomers are generally low melting solids or liquids.

The first oligomer may be prepared (e.g., by solution polymerization followed by isolation) and then combined with a separately prepared second component oligomer. Any residual monomer and/or solvents used in the preparation are generally removed by conventional techniques such as distillation, vacuum evaporation, etc., to reduce the residual content to less than 2 wt. %, prior to crosslinking. Depending on the type of coating process to be used, the relative amounts of the oligomer(s) can vary greatly. The polymerizations may be conducted in the presence of suitable solvents such as ethyl acetate, toluene and tetrahydrofuran that are unreactive with the functional groups of the components of the first and second components.

The second component oligomer may be prepared in situ provided that, prior to crosslinking, the residual content is less than 2 wt. %, or the second component oligomer may be separately prepared and added to the oligomer mixture. The crosslinked composition of the invention results from a chain-growth process by reaction of the pendent unsaturated polymerizable groups and the pendent photoinitiator groups. Each of the first and second component oligomers may comprise a mixture of oligomers falling within their respective descriptions.

Polymerization to prepare the crosslinked oligomeric composition can be accomplished by exposing the component oligomer mixture to actinic energy in the presence of the photoinitiator group of the second component oligomer. The amount of the first and second component oligomer may be chosen so that the concentration of photoinitiator groups is from about 0.0001 to about 3.0 pbw, preferably from about 0.001 to about 1.0 pbw, and more preferably from-about 0.005 to about 0.5 pbw, per 100 pbw of the composition.

A coatable oligomer composition may be prepared by combining the first and second oligomer component oligomers. Partial conversion of the two components may be necessary to achieve a thickened solution exhibiting a coatable viscosity of from about 500-10,000 cPs at 22° C., more preferably from about 750 to 7500 cPs.

Once configured into the desired construction, the composition including the first and second oligomer components may be irradiated with activating UV radiation to crosslink the composition. UV light sources can be of two types: 1) relatively low light intensity sources such as blacklights which provide generally 10 mW/cm² or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm², preferably between 15 and 450 mW/cm². Where actinic radiation is used to fully or partially crosslink the polymer composition, high intensities and short exposure times are preferred. For example, an intensity of 600 mW/cm² and an exposure time of about 1 second may be used successfully. Intensities can range from about 0.1 to about 150 mW/cm², preferably from about 0.5 to about 100 mW/cm², and more preferably from about 0.5 to about 50 mW/cm².

Accordingly, relatively thick coatings (e.g., at least about 0.025 mm) can be achieved when the extinction coefficient of the photoinitiator is low. Coatings from of 0.5 or more mm thick are possible and are within the scope of the present invention.

Additional advantages of the photopolymerization method are that 1) heating the composition is unnecessary and 2) photoinitiation is stopped completely when the activating light source is turned off.

If so desired, measuring the refractive index of the composition material especially in bulk can be used to monitor the extent of polymerization. The refractive index changes linearly with respect to conversion. This monitoring method is commonly applied in polymerization kinetics work. See discussions about the method in, for example, G.P. Gladyshev and K. M. Gibov, Polymerization at Advanced Degrees of Conversion, Keter Press, Jerusalem (1970).

When preparing a crosslinked composition of the invention, it may be expedient for the initiated polymerization reactions to proceed to virtual completion, i.e., depletion of the pendent polymerizable functional groups, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds residuals that will remain with the system and inhibit the desired polymerization of the polymer and formation of the crosslinked compositions of the invention. Free radical polymerization inhibitors are often required at processing temperatures of 70° C. and higher for reaction periods of more than about 6 hours.

The crosslinked composition can be characterized as a polymer having a first oligomer chain having at least one pendent hydrophilic moiety and the residue of at least one pendent, ethylenically unsaturated moiety chemically bonded to the residue of a second, pendent ethylenically unsaturated moiety of a second oligomer chain. As a polymeric photoinitiator is used, the polymer may be further characterized as having the residue of at least one pendent, ethylenically unsaturated moiety chemically bonded to the residue of a photoinitiator moiety. Preferably each polymer chain comprises a (meth)acrylate polymer chain. Thus, during exposure to UV energy, the free radical resulting from the photoinitiator (of the second component oligomer) adds to the pendent ethylenically unsaturated moiety to form a crosslink between the oligomer chains upon coupling or propagation with another polymerizable group on another oligomer chain. In general, the present crosslinked composition has effective molecular weight between crosslinks, ($M_c$), of greater than or equal to 1,000 and preferably greater than 3,000. Effective molecular weight between crosslinks (Mc), may be measured by dynamic mechanical analysis.

The degree of crosslinking may be easily controlled by the number and concentration of pendent unsaturated groups and by the number and concentration of photoinitiator groups that are pendent on the oligomer(s). The ratio of photoinitiator groups to pendent, free-radically polymerizable, unsaturated groups can vary from about 1:10,000 to 1:1, depending on the degree of crosslinking desired. Generally the smaller the $M_c$, the lower the elasticity and hence harder the crosslinked composition.

When the composition of the invention is used to prepare hydrophilic gel materials for medical applications, the gel can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocalne, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material of the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 84% per ASTM D1003-00). Typically, the amount of hydrocolloid, if used, is less than about 5 wt. %, based on the total weight of the gel material.

Other additives that can be incorporated into the gel material of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and alpha-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the gel material of the present invention is substantially free of residuals, including water. This is advantageous at least because special packaging is not required. Furthermore, residuals can migrate to other parts of a dressing, for example, which can be detrimental to the integrity of the dressing, or into the body of the patient on which the dressing is disposed.

Optionally, the gel material may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e., expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges that are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different than the pattern on the facing surface of the gel material, as can the size of the pattern elements. Further, the individual elements on either surface of the gel material may be protuberances extending form the surface, or may be depressions in the surface.

An optional patterned surface may be imparted to the gel material by conventional molding techniques. Alternatively, a desired pattern may be imparted using an embossing technique. Examples of such techniques are described in U.S. Pat. No. 6,566,575 (Burton et al.).

If desired, the gel material may be in direct contact with the wound and/or skin surface. However, direct contact may be provided by other suitable hydrocolloid and hydrogel absorbent materials as well.

In a preferred medical article, the gel material forms a layer that is generally about 250 micrometers (i.e., microns) to about 5000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the oligomeric composition. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 200 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e., fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations means for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyetheramide, polyurethanes, chlorinated polyethylene, styrene/butadiene block copolymers (KRATON brand thermoplastic rubber, Shell Chemical Company, Houston, Tex.) and poly(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B.F. Goodrich, Cleveland, Ohio, elastomeric polyester such as those available under the trade designation HYTREL from E.I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 $g/m^2/24$ hrs, preferably about 3000 to 4000 $g/m^2/24$ hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in International Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat-sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. Nos. 4,499,896 (Heinecke); 4,598,004 (Heinecke); and 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive that can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration —A—B—A— wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. Nos. 6,198,016 B1 (Lucast et al.), 6,518,343 (Lucast et al.), and 6,441,092 (Gieselman et al); multilayered adhesives as disclosed in U.S. Pat. No. 6,461,467 (Blatchford et al.). A particularly preferred adhesive includes 15 wt. % acrylic acid, 15 wt. % methoxypolyethylene oxide 400 acrylate, 70 wt. % isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e., the surface in contact with the wound site, whether it is the front surface of the facing or backing layers) so as to not impede the flow of exudate to the gel layer, i.e., the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYSLIK S-8004, 83 pound (135.4 g/m$^2$) bleached silicone release paper supplied by H.P. Smith Co., Chicago, Ill., and 80 pound (130.5 g/m$^2$) bleached two-sided silicone coated paper (2-80-BKG-157) supplied by Daubert Chemical Co., Dixon, Ill.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. Nos. 5,531,855 (Heinecke et al.) and 5,738,642 (Heinecke et al.).

EXAMPLES

Unless otherwise noted, all reagents and solvents were or can be obtained from Aldrich Chemical Co., Milwaukee, Wis.

As used herein,

"BHT" refers to butylated hydroxy toluene, also know as 2,6-di-tert-butyl-4-methyl phenol;

"HEMA" refers to 2-hydroxyethyl methacrylate, available from Mitsubishi Rayon Co., Ltd., Tokyo, Japan;

"MPEG" refers to polyethylene glycol methyl ether methacrylate, Mw=454 g/mol, available from Osaka Organic Chemical Industry, Ltd., Osaka, Japan;

"VDM" refers to vinyl dimethyl azlactone, available from Groupe SNPE, Paris, France;

"DMACM" refers to N,N'-dimethyl acrylamide;

"NVA" refers to N-vinyl acetamide;

"MPEG-1000" refers to polyethylene glycol methyl ether methacrylate, Mw=1100 g/mol;

"DBU" refers to 1,8-diazabicyclo[5.4.0]undec-7-ene;

"IEM" refers to 2-isocyanatoethyl methacrylate;

"AIBN" refers to 2,2'-azobis(isobutyronitrile);

DAROCUR ZLI-3331 refers to 2-propenoic acid, 2-[4-(2-hydroxy-2-methyl-1-oxopropyl)phenoxy]ethyl ester, and was obtained from Ciba-Geigy, Hawthorne, N.Y.;

VAZO 52 refers to 2,2-azobis(2,4-dimethylpentanenitrile), available from E.I. du Pont de Nemours and Co., Wilmington, Del.;

IRGACURE 184 (IG184) refers to 1-hydroxycylcohexyl phenyl ketone, available from Ciba Specialty Chemical Corp, Tarrytown, N.Y.

Methods

The number average molecular weight ($M_n$) of each composition was determined using gel permeation chromatography (GPC).

The absorbency of each exemplary composition was determined by immersing a weighed 3 cm diameter disk of the composition, each having a thickness of approximately 1.1 mm, in approximately 200 mL of 0.9 wt. % aqueous NaCl.

The weight of each sample disk was recorded as "dry weight." After 24 hours, each sample disk was removed from the solution and the excess liquid was allowed to drip off of the disk for 1 minute. The sample disk was again weighed and this weight was recorded as "wet weight." The absorbency of each sample disk was calculated as the increase in sample weight, expressed as a percentage of the dry weight, according to the formula 100*(wet weight-dry weight)/dry weight.

Preparatory Example 1

A hydrophilic copolymer with photoinitiator pendant groups was synthesized by charging an amber glass bottle with 99.0 g of MPEG, 1.0 g of DAROCUR ZLI-3331, 0.1 g of α-methyl styrene, 0.4 g of VAZO 52 and 100 g of ethyl acetate. The contents of the bottle were purged with N2 for 20 minutes and the bottle was capped, using poly(tetrafluoroethylene) thread tape (available from 3M Company, St. Paul, Minn.) between the cap and the threads of the bottle. The bottle was placed in a Model LLF LAUNDER-O-METER (available from Atlas Electric Devices Co., Chicago, Ill.), with the water bath temperature set at 60° C., for 16 hours. The resulting polymer had a $M_n$ of 36,900 as determined by GPC.

Preparatory Example 2

A hydrophilic copolymer with photoinitiator pendant groups was synthesized by charging an amber glass bottle with 65.0 g of MPEG, 35.0 g of HEMA, 1.0 g of DAROCURE ZLI-3331, 4.0 g of α-methylstyrene, 0.4 g of AIBN and 90 g of ethyl acetate. The contents of the bottle were purged with nitrogen gas for 20 minutes and the bottle was capped, using poly(tetrafluoroethylene) thread tape. The bottle was placed in a water bath shaker at 65° C. for 24 hours. The resulting polymer had a M of 15,700 as determined by GPC.

Preparatory Example 3-7

A series of hydrophilic copolymers were synthesized by charging 5 amber glass bottles with different weight proportions of hydrophilic monomers and α-methyl styrene as shown in Table 1. Sufficient ethyl acetate was added to each bottle so that the total monomer concentration was 50 wt. %. VAZO 52 (0.4 g) was added to each bottle. The contents of each bottle were purged with nitrogen gas for 20 minutes and the bottle was capped, using poly(tetrafluoroethylene) thread tape. Each bottle was placed in a Model LLF LAUNDER-O-METER, with the water bath temperature set at 60° C., for 16 hours. Compositions and $M_n$ values for Preparatory Examples 3-7 are shown in Table 1.

TABLE 1

| Preparatory Examples 3-7 | | | | | | | |
|---|---|---|---|---|---|---|---|
| Preparatory Example | MPEG (g) | HEMA (g) | DMACM (g) | NVA (g) | MPEG-1000 (g) | Alpha-methylstyrene (g) | Mn |
| 3 | 93.7 | 4.9 | | | | 1.0 | 43,000 |
| 4 | 98.5 | 1.0 | | | | 0.1 | 34,900 |
| 5 | 64.1 | 4.9 | 29.6 | | | 1.0 | 37,100 |
| 6 | 64.1 | 4.9 | | 29.6 | | 1.0 | 23,800 |
| 7 | | 1.0 | | | 98.5 | 0.1 | 13,200 |

Preparatory Examples 8-12

Each solution of the products of Preparatory Examples 3-7 was combined with VDM and a catalytic amount of DBU in an amber bottle. The bottle was agitated in a heated shaker water bath at 60° C. for 16 hours. The data are given in Table 2.

TABLE 2

| Preparatory Examples 8-12 | | | |
|---|---|---|---|
| Preparatory Example | Product from Preparatory Example (Component A) | Wt. Component A (g) | Wt. VDM (g) |
| 8 | 3 | 40.00 | 1.07 |
| 9 | 4 | 40.00 | 0.21 |
| 10 | 5 | 40.00 | 1.07 |
| 11 | 6 | 40.00 | 1.07 |
| 12 | 7 | 6.00 | 0.03 |

Preparatory Examples 13-15

Each solution of the products of Preparatory Examples 3-5 was combined with IEM and a catalytic amount of dibutyltin dilaurate in an amber bottle. The bottle was agitated in a heated shaker water bath at 60° C. for 16 hours. The data are given in Table 3.

TABLE 3

| Preparatory Examples 13-15 | | | |
|---|---|---|---|
| Preparatory Example | Product from Preparatory Example (Component A) | Wt. Component A (g) | Wt. IEM (g) |
| 13 | 3 | 40.00 | 1.19 |
| 14 | 4 | 40.00 | 0.21 |
| 15 | 5 | 40.00 | 1.19 |

Preparatory Example 16-19

A series of hydrophilic copolymers were synthesized by charging 4 amber glass bottles with different weight proportions of hydrophilic monomers and α-methyl styrene, and VAZO 52 (0.4 g). Sufficient ethyl acetate was added to each bottle so that the total monomer concentration was 50 wt. %. The contents of each bottle were purged with nitrogen gas for 20 minutes and the bottle was capped, using poly(tetrafluoroethylene) thread tape. Each bottle was placed in a Model LLF LAUNDER-O-METER, with the water bath temperature set at 60° C., for 16 hours. Compositions and $M_n$ values for Examples 16-19 are shown in Table 4.

TABLE 4

Preparatory Examples 16-19

| Preparatory Example | MPEG (g) | VDM (g) | DMACM (g) | MPEG-1000 (g) | Alpha-methylstyrene (g) | Mn |
|---|---|---|---|---|---|---|
| 16 | 93.7 | 4.9 | | | 1.0 | 42,400 |
| 17 | 98.5 | 1.0 | | | 0.1 | 38,500 |
| 18 | 64.1 | 4.9 | 29.6 | | 1.0 | 45,300 |
| 19 | | 1.0 | | 98.5 | 0.1 | 13,700 |

Preparatory Examples 20-23

Each solution of the products of Preparatory Examples 16-19 was combined with different proportions of HEMA, BHT (100 ppm), and a catalytic amount of DBU in an amber bottle. The bottle was agitated in a heated shaker water bath at 60° C. for 16 hours. The data are given in Table 5.

TABLE 5

Preparatory Examples 20-23

| Preparatory Example | Product from Preparatory Example (Component A) | Wt. Component A (g) | Wt. HEMA (g) |
|---|---|---|---|
| 20 | 16 | 40.00 | 0.94 |
| 21 | 17 | 40.00 | 0.19 |
| 22 | 18 | 40.00 | 0.94 |
| 23 | 19 | 10.00 | 0.05 |

Preparatory Example 24-29

A hydrophilic copolymer was synthesized by charging an amber glass bottle with 65.1 g of MPEG, 35.0 g of HEMA, 4.0 g of α-methyl styrene, 0.4 g of AIBN and 90 g of ethyl acetate. The contents of the bottle were purged with nitrogen gas for 20 minutes and the bottle was capped, using poly(tetrafluoroethylene) thread tape. The polymerization bottle was placed in a water bath shaker at 65° C. for 24 hours. The resultant polymer had a $M_n$ of 12,200 as determined by GPC.

A series of copolymers with pendent ethylenic unsaturation were prepared by reacting portions of this copolymer with different weight proportions of IEM and a catalytic amount of dibutyltin dilaurate. The proportion of IEM in these copolymers, expressed as the weight percentage of IEM in the product, are given in Table 6. This step was performed by agitating the mixture at room temperature for 48 hours.

TABLE 6

Preparatory Examples 24-29

| Preparatory Example | % by Weight IEM |
|---|---|
| 24 | 0.5 |
| 25 | 1.0 |
| 26 | 2.0 |
| 27 | 3.7 |
| 28 | 9.0 |
| 29 | 17.3 |

Example 30-61

A series of films were prepared by mixing either IG184 or different proportions of the solution of the product of Preparatory Example 1 (referred to as Component A in Table 7) with different proportions of each solution of the product of Preparatory Examples 8-15 (referred to as Component B in Table 7). The mixed solutions were separately coated onto a sheet of poly(ethylene terephthalate) (PET) release liner, such as those available under the trade designation "CLEAR-SIL", available from CPFilms, Martinsville, Va., and the solvent was evaporated by heating the coatings in an oven at 50° C. for 4 hours. Another layer of PET release liner was then placed on top of the film, providing a coated film between two sections of PET release liner. This was irradiated for 30 minutes using a Sylvania F40/350 BL lamp (available from OSRAM SYLVANIA, Danvers, Mass.) with the sample approximately 2.5 cm from the lamp. The composition and absorbency of the films are given in Table 7. For Table 7, when absorbency could not be obtained because the sample lacked sufficient strength to be transferred from the solution, the absorbency is given as "N/A."

TABLE 7

Examples 30-61

| Example | Component A Preparatory Example Number (wt. %) | Component B Preparatory Example Number (wt. %) | Absorbency |
|---|---|---|---|
| 30 | 1 (50) | 8 (50) | N/A |
| 31 | 1 (30) | 8 (70) | 119 |
| 32 | 1 (70) | 8 (30) | N/A |
| 33 | Comparative Example (IG184, 0.2) | 8 (99.8) | N/A |
| 34 | 1 (50) | 9 (50) | 479 |
| 35 | 1 (30) | 9 (70) | 396 |
| 36 | 1 (70) | 9 (30) | 516 |
| 37 | Comparative Example (IG184, 0.2) | 9 (99.8) | 620 |
| 38 | 1 (50) | 10 (50) | 410 |
| 39 | 1 (30) | 10 (70) | N/A |
| 40 | 1 (70) | 10 (30) | 536 |

TABLE 7-continued

Examples 30-61

| Example | Component A Preparatory Example Number (wt. %) | Component B Preparatory Example Number (wt. %) | Absorbency |
|---|---|---|---|
| 41 | Comparative Example (IG184, 0.2) | 10 (99.8) | N/A |
| 42 | 1 (50) | 11 (50) | N/A |
| 43 | 1 (30) | 11 (70) | N/A |
| 44 | 1 (70) | 11 (30) | 453 |
| 45 | Comparative Example (IG184, 0.2) | 11 (99.8) | N/A |
| 46 | 1 (50) | 12 (50) | 781 |
| 47 | 1 (30) | 12 (70) | 530 |
| 48 | 1 (70) | 12 (30) | 528 |
| 49 | Comparative Example (IG184, 0.2) | 12 (99.8) | 490 |
| 50 | 1 (50) | 13 (50) | 349 |
| 51 | 1 (30) | 13 (70) | 183 |
| 52 | 1 (70) | 13 (30) | 365 |
| 53 | Comparative Example (IG184, 0.2) | 13 (99.8) | 186 |
| 54 | 1 (50) | 14 (50) | 355 |
| 55 | 1 (30) | 14 (70) | 286 |
| 56 | 1 (70) | 14 (30) | 507 |
| 57 | Comparative Example (IG184, 0.2) | 14 (99.8) | 229 |
| 58 | 1 (50) | 15 (50) | 358 |
| 59 | 1 (30) | 15 (70) | 273 |
| 60 | 1 (70) | 15 (30) | 519 |
| 61 | Comparative Example (IG184, 0.2) | 15 (99.8) | 245 |

Examples 62-77

A series of films were prepared by mixing either IG184 or different proportions of the solution of the product of Preparative Example 1 (referred to as Component C in Table 8) with different proportions of each solution of the product of Preparative Examples 20-23 (referred to as Component D in Table 8). The mixed solutions were separately coated onto poly(ethylene terephthalate) (PET) release liner, such as those available under the trade designation "CLEARSIL", available from CPFilms, Martinsville, Va., and the solvent was evaporated by heating the coatings in an oven at 50° C. for 4 hours. Another layer of PET release liner was then placed on top of the film, providing a coated film between two sections of PET release liner. This was irradiated as described in Examples 30-61. For Table 8, when absorbency could not be obtained because the sample lacked sufficient strength to be transferred from the solution, the absorbency is given as "N/A."

TABLE 8

Examples 62-77

| Example | Component C Preparatory Example Number (wt. %) | Component D Preparatory Example Number (wt. %) | Absorbency |
|---|---|---|---|
| 62 | 1 (50) | 20 (50) | N/A |
| 63 | 1 (30) | 20 (70) | N/A |
| 64 | 1 (70) | 20 (30) | 297 |
| 65 | Comparative Example (IG184, 0.2) | 20 (99.8) | 105 |
| 66 | 1 (50) | 21 (50) | 540 |
| 67 | 1 (30) | 21 (70) | 574 |
| 68 | 1 (70) | 21 (30) | 655 |
| 69 | Comparative Example (IG184, 0.2) | 21 (99.8) | 720 |
| 70 | 1 (50) | 22 (50) | 452 |
| 71 | 1 (30) | 22 (70) | 182 |
| 72 | 1 (70) | 22 (30) | 379 |
| 73 | Comparative Example (IG184, 0.2) | 22 (99.8) | 119 |
| 74 | 1 (50) | 23 (50) | 399 |
| 75 | 1 (30) | 23 (70) | 325 |
| 76 | 1 (70) | 23 (30) | 555 |
| 77 | Comparative Example (IG184, 0.2) | 23 (99.8) | 391 |

Examples 78-83

A series of films were made by mixing equal weights of a solution of each of the products from Preparative Example 24-29 (identified as Component E in Table 9) with a solution of the product of Preparative Example 2. The resultant solutions were separately coated onto poly(ethylene terephthalate) (PET) release liner, such as those available under the trade designation "CLEARSIL", available from CPFilms, Martinsville, Va., and the solvent was evaporated by heating the coatings in an oven at 50° C. for 4 hours. Another layer of PET release liner was then placed on top of the film, providing a coated film between two sections of PET release liner. This was irradiated as described in Examples 30-61. The data are given in Table 9.

TABLE 9

Examples 78-83

| Example | Component E (Preparatory Example Number) | Absorbency |
|---|---|---|
| 78 | 24 | 327 |
| 79 | 25 | 310 |
| 80 | 26 | 239 |
| 81 | 27 | 212 |
| 82 | 28 | 118 |
| 83 | 29 | 75 |

The invention claimed is:

1. An absorbent dressing comprising a crosslinked hydrophilic gel absorbent layer of a crosslinkable oligomer composition comprising:
    (1) a first component oligomer comprising a plurality of polymerized monomer units having pendent, free-radically polymerizable functional groups, and a plurality of polymerized monomer units having pendent, hydrophilic poly(alkylene oxide) groups; and
    (2) a second component oligomer comprising a plurality of polymerized monomer units having pendent, photoinitiator groups.

2. The absorbent dressing of claim 1 comprising:
    a permeable facing layer,
    a backing layer bonded to said facing layer at the periphery, and
    a hydrophilic gel absorbent layer disposed between the backing and facing layer.

3. The absorbent dressing of claim 2 having a layer of pressure sensitive adhesive on at least a portion of the front surface of the facing layer.

4. The absorbent dressing of claim 2, wherein the gel layer further comprises a pharmacologically active agent.

5. The absorbent dressing of claim 2, wherein the gel layer further comprises a hydrocolloid.

6. The absorbent dressing of claim 2, wherein the gel layer further comprises a patterned surface.

7. The absorbent dressing of claim 1 having a residuals content of less than 2 wt. %.

8. The absorbent dressing of claim 1, wherein said pendent polyalkylene oxide groups of said first component oligomer is of the formula:

—(CH($R^1$)—CH$_2$—O)—$R^2$ wherein $R^1$ is a H or a $C_1$ to $C_4$ alkyl group, $R^2$ is H, a C to $C_4$ alkyl group, aryl, or combinations thereof, and m is from 2 to 100.

9. The absorbent dressing of claim 1, wherein said pendent poly(alkylene oxide) group is a poly(ethylene oxide) (co)polymer.

10. The absorbent dressing of claim 1, wherein said pendent poly(alkylene oxide) group is a poly(ethylene oxide-co-propylene oxide) copolymer.

11. The absorbent dressing of claim 1, wherein said second component oligomer further comprises a plurality of polymerized monomer units having pendent, hydrophilic poly(alkylene oxide) groups.

12. The absorbent dressing of claim 1, wherein said first oligomer having pendent unsaturated polymerizable groups is prepared by the reaction of an oligomer having a plurality of pendent reactive functional groups with an unsaturated compound having co-reactive functional groups.

13. The absorbent dressing of claim 1 which comprises: (a) from 0.01 to 99.9 parts by weight of said first component oligomer, and (b) from 99.9 to 0.1 parts by weight of said second component oligomer, wherein the composition, when crosslinked, can absorb at least 50 wt. % water.

14. The absorbent dressing of claim 1, wherein said first component oligomer comprises (a) from 20 to 99 parts by weight of polymerized monomer units derived from an ethylenically-unsaturated monomer having a pendent poly(alkylene oxide) group; (b) from 0.1 to 35 parts by weight of polymerized monomer units derived from an ethylenically-unsaturated monomer having a pendent polymerizable functional group; (c) from 0 to 50 parts by weight of polymerized monomer units derived from a polar monomer; (d) from 0 to 20 parts by weight of polymerized monomer units derived from a hydrophobic monomer; and (e) from 0 to 10 parts by weight of at least one other monomer.

15. The absorbent dressing composition of claim 14, wherein said polar monomer c), when present, is selected from the group consisting of substituted (meth)acrylamides, N-vinyl pyrrolidone, N-vinyl caprolactam, acrylonitrile, N-vinyl acetamide, tetrahydrofurfuryl acrylate, acrylamides, and mixtures thereof.

16. The absorbent dressing of claim 1, wherein the second oligomer component comprises (a) from 20 to 99 parts by weight of polymerized monomer units having pendent, hydrophilic poly(alkylene oxide) groups; (b) from 0.1 to 25 parts by weight of polymerized monomer units derived from an ethylenically-unsaturated monomer having a pendent photoinitiator group; (c) from 0 to 25 parts by weight of polymerized monomer units derived from an ethylenically-unsaturated monomer having a pendent polymerizable group; (d) from 0 to 20 parts by weight of hydrophobic monomers; (e) from 0 to 50 parts by weight of polymerized monomer units derived from a polar monomer; and (f) from 0 to 40 parts by weight, preferably less than 25 parts by weight, of at least one other monomer.

17. The absorbent dressing of claim 1, wherein hydrophilic gel layer is capable of absorbing 50% by weight water.

18. The absorbent dressing of claim 1, wherein hydrophilic gel layer contains one or more pharmacologically active agents.

19. The absorbent dressing of claim 1, wherein hydrophilic gel layer is 250 micrometers to 5000 micrometers in total thickness.

20. The absorbent dressing of claim 2, wherein the backing layer is a fluid control film having at least one microstructures-bearing surface with channels that permit directional control of a liquid.

* * * * *

UNITED STATES PATENT AND TRADEMARK OFFICE
CERTIFICATE OF CORRECTION

PATENT NO. : 7,659,323 B2  Page 1 of 2
APPLICATION NO. : 12/555354
DATED : February 9, 2010
INVENTOR(S) : Kevin M. Lewandowski It is certified that error appears in the above-identified patent and that said Letters Patent is hereby corrected as shown below:

Column 6,
Line 4, delete "CH-Q)" and insert -- $CH_2$-Q$)_m$ --.
Line 9, delete "CO" and insert -- $CO_2$ --.

Column 9,
Lines 47 and 48, delete

" 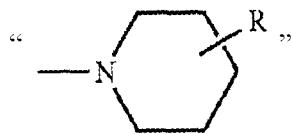 "

and insert

--  --.

Column 11,
Line 18, delete "T" and insert -- $T_g$ --.
Line 20, delete "C13" and insert -- $C_{13}$ --.
Line 42, delete "T" and insert -- $T_g$ --.

Column 16,
Line 9, delete "(Mc)," and insert -- $(M_c)$, --.
Line 36, delete "prilocalne," and insert -- prilocaine, --.

Column 20,
Line 56, after "international" insert -- Publication No. WO 00/42958. --.

Column 23,
Line 47, delete "N2" and insert -- $N_2$ --.
Line 67, delete "M" and insert -- $M_n$ --.

Column 24,
Line 3, Table 1, delete "Mn" and insert -- $M_n$ --.

Column 25,
Line 4, Table 1, delete "Mn" and insert -- $M_n$ --.

CERTIFICATE OF CORRECTION (continued)
U.S. Pat. No. 7,659,323 B2

Column 29,
Line 15, delete "O)" and insert -- $O)_m$ --.
Line 16, delete "C" and insert -- $C_1$ --.

Signed and Sealed this

Twentieth Day of April, 2010

David J. Kappos
*Director of the United States Patent and Trademark Office*